United States Patent

Wallén

[11] Patent Number: 6,035,851
[45] Date of Patent: Mar. 14, 2000

[54] METHOD AND DEVICE FOR MONITORING THE CONDITION OF A FILTER IN A VENTILATOR

[75] Inventor: Lars Wallén, Spånga, Sweden

[73] Assignee: Siemens-Elema AB, Solna, Sweden

[21] Appl. No.: 08/941,307

[22] Filed: Sep. 30, 1997

[30] Foreign Application Priority Data

Oct. 3, 1996 [SE] Sweden ................................ 9603612-4

[51] Int. Cl.$^7$ ................................................ A61M 16/00
[52] U.S. Cl. ................................ 128/202.22; 128/205.12; 128/205.27; 128/205.23
[58] Field of Search ........................ 128/202.22, 205.12, 128/205.21, 205.23, 205.27, DIG. 25, 204.22; 73/23.22, 866, 38, 40; 95/19, 20; 96/421

[56] References Cited

U.S. PATENT DOCUMENTS

| | | | |
|---|---|---|---|
| 3,771,365 | 11/1973 | Schempp | 96/421 |
| 4,122,839 | 10/1978 | Franetzki et al. | 128/DIG. 25 |
| 4,449,392 | 5/1984 | Huschke | 73/40 |
| 4,751,501 | 6/1988 | Gut | 96/421 |
| 5,337,739 | 8/1994 | Lehman | 128/205.23 |
| 5,347,843 | 9/1994 | Orr et al. | 73/3 |
| 5,413,097 | 5/1995 | Birenheide et al. | 128/202.22 |
| 5,477,731 | 12/1995 | Mouton | 73/38 |
| 5,659,296 | 8/1997 | Debe | 128/202.22 |

FOREIGN PATENT DOCUMENTS

| | | |
|---|---|---|
| PS 24 04 452 | 9/1984 | Germany . |
| PS 41 17 422 | 11/1992 | Germany . |
| 2 253 572 | 9/1992 | United Kingdom . |
| 2 278 295 | 11/1994 | United Kingdom . |

*Primary Examiner*—John G. Weiss
*Assistant Examiner*—V. Srivastava
*Attorney, Agent, or Firm*—Hill & Simpson

[57] ABSTRACT

A method and device for monitoring the condition of at least one filter arranged in a flow path of a ventilator. Flow measurement signals are obtained from a first flow meter and a second flow meter and pressure signals are obtained from a first pressure meter and a second pressure meter. When a filter in the inspiratory section of the ventilator is to be tested, flow through the filter and the drop in pressure across the filter are determined from the pressure measured by the first pressure meter and the second pressure meter. If the drop in pressure in relation to the flow lies within predefined limits, the filter is deemed to be serviceable. In a corresponding manner, another filter in the expiratory line can be tested, wherein flow through the filter is determined by the second flow meter.

6 Claims, 1 Drawing Sheet

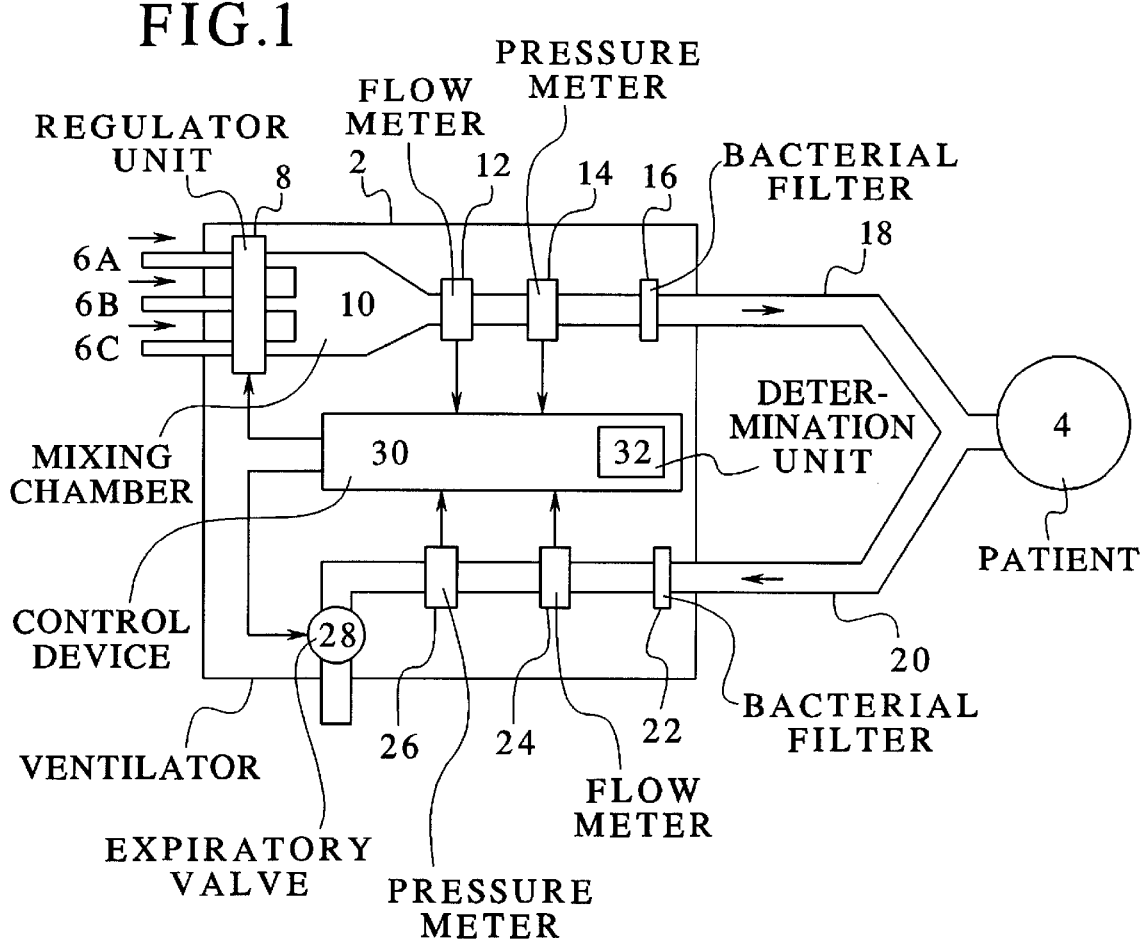
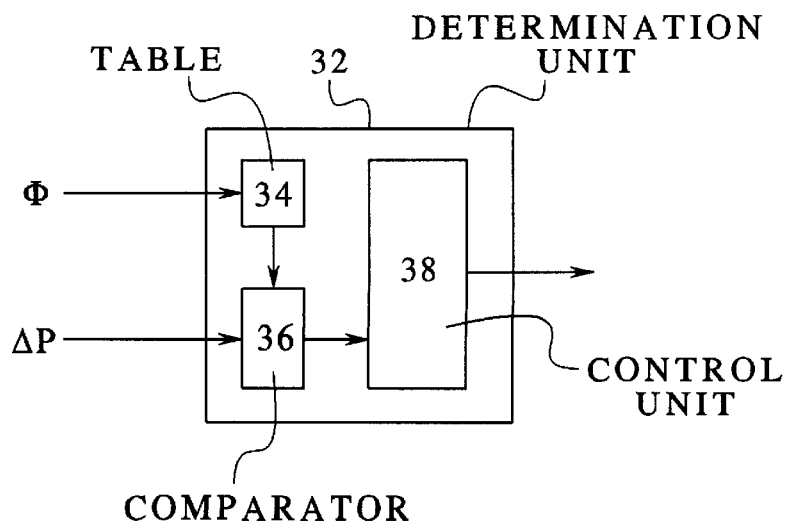

METHOD AND DEVICE FOR MONITORING THE CONDITION OF A FILTER IN A VENTILATOR

BACKGROUND OF THE INVENTION

1. Field of the Invention

The present invention relates to a method for monitoring the condition of at least one filter arranged in a flow path of a ventilator.

The present invention also relates to a device for monitoring the condition of at least one filter in a flow path of a ventilator, and to a ventilator containing such a device.

2. Description of the Prior Art

Filters of various kinds are frequently used in ventilators. In respiratory treatment, for example, bacterial filters are often employed to reduce the risk of a spread of infection between patients when the ventilator is connected to a new patient. Bacterial filters can also be used to reduce the risk of exposing patients to bacteria carried in inspiratory air and the escape of bacteria in expiratory air into ambient air. Bacterial filters can also be used to protect equipment from "contaminants", such as medication and body fluids, in expiratory air.

The use of disposable filters, which are discarded after each use and replaced with new filters when a new patient is to be connected to the ventilator, is relatively common. Disposable filters represent a major cost to hospitals and also have an environmental impact. Bacterial filters are available which can be autoclaved and, accordingly, used for a number of patients, with inter-patient autoclaving to disinfect the filter. The disadvantage of reusing a filter, however, is that it ultimately becomes clogged, thereby increasing resistance to flow in flow lines. A clogged filter can also increase pressure in the lungs of the patient connected to the ventilator and thus increase the risk of injury. Filter leakage after the filter has been autoclaved a number of times is an additional risk. Therefore, these filters are often discarded, while still fully serviceable, for safety reasons and are therefore not put to optimum use.

Disposable filters can naturally leak or become clogged as well, especially after a long period of use.

SUMMARY OF THE INVENTION

An object of the present invention is to provide a method for monitoring the condition of a filter in order to optimize filter life without any risk to patients. The check as to condition especially applies to filters which can be used repeatedly with interpatient cleaning/disinfection.

Another object of the invention is to provide a device for monitoring the condition of filters in the respective flow paths of ventilators.

An additional object of the invention is to provide a ventilator with a built-in check as to filter condition.

The above objects are achieved in a method for monitoring the condition of at least one filter arranged in a flow path of a ventilator in accordance with the invention wherein the pressure drop across the filter is determined from existing pressure meters in the breathing equipment, flow through the filter is determined from existing flow meters in the breathing equipment, a relationship between the pressure drop and flow is established (identified), and the filter is deemed to be serviceable as long as the pressure drop lies within predetermined limits in relation to the flow.

A filter always presents an impediment or resistance to the flow of a gas passing through the filter. This causes a drop in pressure which is related to both the filter's resistance and to flow. A clogged filter presents increased resistance, so the pressure drop for a given flow will increase across the clogged filter. Some degree of clogging is tolerable, but the filter must be replaced when clogging become excessive. The magnitude of the pressure drop for every flow therefore becomes a measure of the condition of the filter.

The use of existing meters for obtaining pressure drop and flow reduces the number of necessary elements to a minimum. Since all meters require calibration, service and cleaning, these operations are also minimized.

A device for monitoring the condition of at least one filter in a flow path of a breathing apparatus in accordance with the invention has a determination unit, which is connectable to existing pressure meters and at least one flow meter in the ventilator for receiving measurement signals from the pressure meters and flow meter(s), the determination unit determining the condition of the filter based on the pressure drop across the filter and flow through the filter according to the above-described method.

The above objects are also achieved in a ventilator having a device as described above operating according to the method described above.

DESCRIPTION OF THE DRAWINGS

FIG. 1 shows an embodiment of breathing equipment according to the invention.

FIG. 2 shows one embodiment of a device for checking a condition of a filter according to the invention.

DESCRIPTION OF THE PREFERRED EMBODIMENTS

FIG. 1 shows a ventilator 2 connected to a patient 4 for supplying a respiratory gas to the lungs of the patient 4. The gas components jointly forming the respiratory gas are delivered to the ventilator 2 via a first gas connector 6A, a second gas connector 6B and a third gas connector 6C. The different gas components are regulated in a regulator unit 8 and then are mixed in a mixing chamber 10. The mixed respiratory gas then passes through a first flow meter 12, a first pressure meter 14 and a first bacterial filter 16, before being carried to the patient 4 via an inspiratory line 18. When the patient 4 exhales, respiratory gas is carried from the patient 4 through an expiratory line 20 back to the ventilator 2, where it is released to the ambient atmosphere. The respiratory gas passes through a second bacterial filter 22, a second flow meter 24, a second pressure meter 26 and an expiratory valve 28. All the functions in the ventilator 2 are controlled by a control device 30.

The flow information obtained from the first flow meter 12 can be obtained instead by flow measurements made by existing flow meters in the regulator unit 8, which are made in order to regulate flows through the respective gas connectors 6A, 6B and 6C. The sum of the gas component flows then becomes the flow of the respiratory gas. In the corresponding manner, the function performed by the first pressure meter 14 can be replaced with existing pressure meters in the regulator unit 8.

A calculation unit 32 is arranged in the control device 30 for determining, from measured pressures and flows, the condition of the two bacterial filters 16 and 22. When the patient 4 inhales and gas is only carried through the inspiratory line 18 to the patient 4, flow measurement values from the first flow meter 12 and pressures measured by the first pressure meter 14 and the second pressure meter 26 are used.

The difference in pressure constitutes the drop in pressure across the first filter 16. The calculation unit 32 then relates the drop in pressure to the flow, and the first bacterial filter 16 is deemed to be fully serviceable if the drop in pressure lies within defined limits in relation to the flow.

If the drop in pressure is too large in relation to the flow, the first bacterial filter 16 is deemed to be too clogged and should therefore be replaced. If the drop in pressure in relation to flow suddenly falls during measurement over a number of consecutive inspirations, the first bacterial filter 16 is probably leaking and should therefore be replaced.

In a corresponding manner, the second bacterial filter 22 can be tested during expiration when gas only flows in the expiratory line 20. The flow is then determined by the second flow meter 24, and the drop in pressure is determined from the pressures measured by the first pressure meter 14 and the second pressure meter 26.

If pressure drop rises suddenly to a very high value, there may be a blockage in the tubing (tubes being bent or compressed).

FIG. 2 shows one way in which the determination unit 32 can relate the drop in pressure to the flow. The measured flow ø is used as an input signal in a table 34. The table 34 contains information on the relationship between flow and pressure for a faultless bacterial filter, e.g. in the form of a measured flow-pressure curve for the specific filter type in question. The filter to be monitored can be supplied with a bar code or the like which is read when the filter is installed. The correct curve is then automatically used by the determination unit 32. Certain safety limits, within which the filter is deemed to be serviceable, are also provided for the recorded curve. These safety margins can be established by tests of each filter type. The output signal from the table 34 then automatically becomes a pressure drop range which is sent to a comparator unit 36. The comparator unit 36 also uses as an input signal the pressure drop measured at the flow serving as the input signal for the table 34. The measured drop in pressure can then be compared in the comparator 36 to the upper limit and lower limit of the pressure drop range. As long as the pressure drop remains within the two limits, the filter can be regarded as serviceable. A signal to this effect is sent to a control unit 38 and can be shown on a display, such as by illuminating a green diode or lamp, or can be used in some other way to provide an indication that the filter is serviceable. If the pressure drop exceeds the upper limit, the filter is clogged, and the comparator 36 sends a signal to this effect to the control unit 38. The control unit 38 can, in turn, issue an alarm or inform the user, via a display or the like, that the filter should be replaced. In a corresponding manner, it can be determined that the filter should be replaced when the pressure drop falls below the lower limit.

Alternatively, the comparator unit 36 may issue a signal only when the filter needs to be changed, irrespective of whether it is clogged or leaking. In digital design, this can be accomplished by the comparator 36 exhibiting a zero at its output terminal as long as the filter is serviceable, i.e., the pressure drop lies within the limits. As soon as the pressure drop becomes greater or less, a one is generated, and an alarm indicating the need to replace the filter can be issued.

If only one filter is arranged in a flow path, e.g. in the inspiratory part of the system, the condition of the filter can be checked in the corresponding manner by measuring pressure before and after the filter and measuring flow through the filter. The drop in pressure can be determined in the same way, i.e., from pressure signals from the inspiratory side and expiratory side respectively.

In order to reduce the risk of temporary disruptions, such as coughing, affecting the check as to clogging, the relevant parameters can be evaluated over a number of breaths and processed statistically. This will also supply information for trend analysis in which remaining filter life can be calculated from changes which are occurring. Trend analysis can be of major value when there is a risk of rapid filter clogging, e.g. when medication or other "contaminants" are suspected of being present, or are known to be present, in the expired air.

Instead of being integrated into the control device 30, the determination unit 32, the table 34 and the comparator 36 could be combined as a separate device, connectable to any ventilator for monitoring filters.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for monitoring a filter disposed in a flow path of a ventilator, comprising the steps of:

providing an inspiratory line in a ventilator;

disposing a first pressure meter in said inspiratory line and determining a pressure in said inspiratory line using said first pressure meter;

providing an expiratory line in said ventilator;

disposing a second pressure meter in said expiratory line and determining a pressure in said expiratory line using said second pressure meter;

disposing a flow meter in at least one of the inspiratory line and the expiratory line and identifying flow in at least one of the inspiratory line and the expiratory line using the flow meter;

disposing a filter in at least one of the inspiratory line and the expiratory line and filtering gas using the filter in at least one of the inspiratory line and the expiratory line;

identifying a pressure drop across said filter from an output of said pressure meter;

identifying flow through said filter from an output of said flow meter;

identifying a relationship between said pressure drop and said flow; and deeming said filter to be serviceable as long as said pressure drop is within predefined limits relative to said flow.

2. A method as claimed in claim 1 comprising the additional step of deeming said filter to be clogged if said pressure drop is larger than a predetermined value relative to said flow.

3. A method as claimed in claim 1 wherein the step of identifying said relationship comprises periodically identifying said relationship during usage of said ventilator, and comprising the additional step of deeming said filter to be leaking if a change in said relationship, larger than a predetermined threshold value, occurs in said relationship during usage of said ventilator.

4. In a ventilator having an inspiratory line, first pressure meter means for determining a pressure in said inspiratory line, an expiratory line, second pressure meter means for determining a pressure in said expiratory line, flow meter means for measuring flow in at least one of said inspiratory line and said expiratory line, and filter means for filtering gas in at least one of said inspiratory line and said expiratory line, the improvement comprising:

means for receiving a signal from said first pressure meter means and said second pressure meter means identifying a pressure drop across said filter means, and for receiving a signal identifying flow through said filter means from said flow meter means;

means for identifying a relationship between said pressure drop and said flow through said filter; and means for identifying a serviceability status of said filter means for deeming said filter means to be serviceable as long as said pressure drop is within predetermined limits relative to said flow.

5. A ventilator as claimed in claim 4 wherein said means for identifying said serviceability status of said filter comprises means for storing a table containing pressure drop ranges for each of a plurality of specific flows employing flow through said filter as an input signal and a pressure drop range as an output signal, and comparator means for comparing said pressure drop to said pressure drop range, said filter being deemed serviceable as long as said pressure drop is within said pressure drop range.

6. A ventilator as claimed in claim 4 wherein said filter means comprises a first filter disposed in said inspiratory line and a second filter disposed in said expiratory line, and wherein said ventilator comprises means for determining a pressure drop across said first filter from a difference between pressures respectively measured by said first pressure meter means and said second pressure meter means during inspiration and a pressure drop across said second filter as a difference between pressures respectively measured by said first pressure meter means and said second pressure meter means during expiration, and wherein said means for identifying a serviceability status of said filter means comprises means for identifying a serviceability status of said first filter from said pressure drop across said first filter and of said second filter by said pressure drop across said second filter.

* * * * *